United States Patent
Roh et al.

(10) Patent No.: US 6,586,616 B1
(45) Date of Patent: Jul. 1, 2003

(54) PROCESS FOR PREPARING (R)-4-CYANO-3-HYDROXYBUTYRIC ACID ESTER

(75) Inventors: Kyoung Rok Roh, Daejeon (KR); Ho Sung Yu, Daejeon (KR); Kyung Il Kim, Daejeon (KR); Won Jang Lee, Daejeon (KR); Dae Il Hwang, Incheon (KR)

(73) Assignee: Samsung Fine Chemicals Co., Ltd., Ulsan (KR)

( * ) Notice: Subject to any disclaimer, the term of this patent is extended or adjusted under 35 U.S.C. 154(b) by 0 days.

(21) Appl. No.: 09/889,978

(22) PCT Filed: Jan. 24, 2000

(86) PCT No.: PCT/KR00/00052

§ 371 (c)(1),
(2), (4) Date: Jul. 25, 2001

(87) PCT Pub. No.: WO00/46186

PCT Pub. Date: Aug. 10, 2000

(30) Foreign Application Priority Data

Feb. 3, 1999 (KR) .......................... 1999/3568

(51) Int. Cl.$^7$ .......................... C07C 253/00
(52) U.S. Cl. .......................... 558/347
(58) Field of Search .......................... 558/347

(56) References Cited

U.S. PATENT DOCUMENTS 5,155,251 A  10/1992  Butler et al.

FOREIGN PATENT DOCUMENTS

EP  573184  5/1993

OTHER PUBLICATIONS

Tetrahedron: asymmetry vol. 4 (1993) pp. 1082–1104. Beard et al. 'Stereoselective Hydrolysis of Nitriles and Amides Under Mild Conditions Using a Whole Cell Catalyst' *see p. 1089 scheme 3.

J. Org. Chem., vol. 61 (1996) pp. 3923–3925. F.J. Lakner et al. 'Chloroperoxidase as Enantioselective Eposidation Catalyst: An Efficient Synthesis of ®–(–)–Mevalonolactone' *see p. 3924 scheme 1 experimental.

Charles R. Degenhardt, Synthesis of Carnitine Homologues. Resactions of Tertiary Amines with Epoxy Esters, J. Org. Chem. 1980, 45, pp. 2763–2766.

Danicle Bianchi et al., Enzymatic Hydrolysis of Alkyl 3,4–Epoxybutyrates. A New Route to ®–(–)–Carnitine Chloride, J. Org. Chem 1988, 53, pp. 104–107.

*Primary Examiner*—Joseph K. McKane
*Assistant Examiner*—Golam M. M. Shameem
(74) *Attorney, Agent, or Firm*—Lowe Hauptman Gilman & Berner, LLP

(57) ABSTRACT

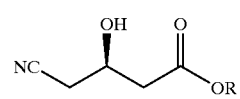

(1)

The present invention relates to a process for preparing (R)-4-cyano-3-hydroxybutyric acid ester derivatives and more particularly, to a process for preparing optically pure (R)-4-cyano-3-hydroxybutyric acid ester derivatives expressed by formula (1) in high yield by performing cyanation and sequential esterification of (S)-3,4-epoxybutyric acid salt as a starting material. In said formula, R represents linear or branched alkyl group with 1~5 carbon atoms or benzyl group.

5 Claims, No Drawings

PROCESS FOR PREPARING (R)-4-CYANO-3-HYDROXYBUTYRIC ACID ESTER

This application is a 371 of PCT/KR00/00052 filed Jan. 29, 2000.

BACKGROUND OF THE INVENTION

1. Field of the Invention

The present invention relates to a process for preparing (R)-4-cyano-3-hydroxybutyric acid esters and more particularly, to a novel process for preparing optically pure (R)-4-cyano-3-hydroxybutyric acid esters expressed by the following formula (1) in high yield by performing cyanation and sequential esterification of (S)-3,4-epoxybutyric acid salt as a starting material,

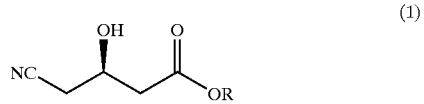

(1)

where in R represents a linear or branched alkyl group having 1~4 carbon atoms or a benzyl group.

2. Description of the Prior Art

Optically active (R)-4-cyano-3-hydroxybutyric acid ester expressed by the following formula (1) is useful as a key intermediate for hypolipidemic agents. Various methods for preparing hypolipidemic agents from optically active (R)-4-cyano-3-hydroxybutyric acid ester have been reported as introduced hereinafter.

U.S. Pat. No. 4,681,893 describes a process for the preparation of hypolipidemic agent, atorvastatin, from (R)-4-cyano-3-hydroxybutyric acid ester.

The use of (R)-4-cyano-3-hydroxybutyric acid ester as starting material is described in preparation of CI-981 which is an inhibitor of 3-hydroxy-3-methylglutarylcoenzyme A(HMG-CoA) reductase in *Tetrahedron Letters*, 33), 2279~2282 (1992).

As described above, there is a need for a simple and inexpensive method for the preparation of (R)-4-cyano-3-hydroxybutyric acid ester due to its usefullness for hypolipidemic agents. A large number of syntheses have been developed. For example, U.S. Pat. No. 4,611,067 describes a method for preparation of (R)-4-cyano-3-hydroxybutyric acid ester by the synthetic pathway from ascorbic acid. Ascorbic acid is degraded to afford 4-bromo-3-hydroxybutyric acid ester through D-threonate potassium salt which is then reacted with an appropriate reagent to protect the hydroxy function to silyl group prior to reaction with sodium cyanide in dimethyl sulfoxide for 16 hours to afford (R)-4-cyano-3-hydroxybutyric acid ester.

However, this conventional method requires multi-step synthesis and long reaction time for cyanation as well as difficulty in removing dimethyl sulfoxide which is used as a solvent. It generates large amount of side-products such as acrylate by dehydration due to the high acidic hydrogen on α-position for the carboxy group and the corresponding acid by hydrolysis of ester groups. In addition, it is not applicable to produce various esters.

SUMMARY OF THE INVENTION

The inventors made extensive efforts to provide more economical and effective preparing methods of (R)-4-cyano-3-hydroxybutyric acid ester which is an essential intermediate for drugs. As a result, it was realized that the use of (S)-3,4-epoxybutyric acid salt as a starting material, followed by cyanation and sequential esterification could provide a novel and inexpensive preparing method of (R)-4-cyano-3-hydroxybutyric acid ester with excellent optical purity and yield.

The introduction of cyano functional group to (S)-3,4-epoxybutyric acid salt in the present invention has not only been tried to afford (R)-4-cyano-3-hydroxybutyric acid ester and but also provided a novelty, applicability and easiness in the method of preparing the same.

Therefore, the purpose of this invention is to provide the synthetic method of optically pure (R)-4-cyano-3-hydroxybutyric acid ester, as the target product, in maximum yield as well as high purity simultaneously inhibiting the side-reaction, hydrolysis or formation of acrylate which are usual problems in the coventional methods.

DETAILED DESCRIPTION OF THE INVENTION

The present invention relates to a process for preparing optically pure (R)-4-cyano-3-hydroxybutyric acid esters expressed by the following formula (1) in high yield by performing cyanation and sequential esterification of (S)-3,4-epoxybutyric acid salt as a starting material,

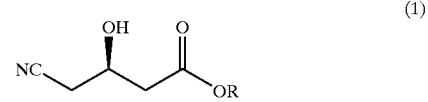

(1)

wherein R represents a linear or branched alkyl group having 1~4 carbon atoms or a benzyl group.

The present invention is explained in more detail as set forth hereunder.

The process enables preparing optically pure (R)-4-cyano-3-hydroxybutyric acid esters economically due to use of aqueous condition in cyanation and introducing various ester groups by esterification without any side reaction.

The procedure described in this invention for the preparation of (R)-4-cyano-3-hydroxybutyric acid ester is briefly shown in the following reaction scheme 1, Scheme 1

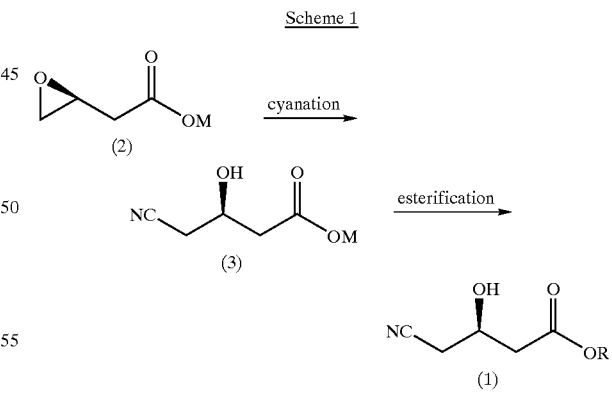

wherein M represents an alkali metal atom, an alkaline earth metal atom or an ammoniun ion; R represents a linear or branched alkyl group having 1 to 4 carbon atoms or a benzyl group.

(S)-3,4-epoxybutyric acid salt used as a starting material in the present invention can be prepared from (S)-4-halo-3hydroxybutyric acid or ester thereof. For example, (S)-3,4-epoxybutyric acid salt is prepared by reacting (S)-4-halo-3hydroxybutyric acid with 1~50% of sodium hydroxide at −50~50° C. for 0.5~10 hours. Over 95% conversion of (S)-4-halo-3-hydroxybutyric acid to (S)-3,4-epoxybutyric acid salt can be detected by NMR.

The formation of a carboxylate anion in the present invention is very important. Generally, a method of (R)-4-cyano-3-hydroxybutyric acid ester is prepared by nucleophilic reaction of cyanide toward (S)-4-halo-3-hydroxybutyric acid ester. A hydrogen on α-position of ester group is so acidic that it is very reactive with a base to produce acrylate by dehydration. However, the formation of a carboxylate anion decreases the acidity of hydrogen on α-position of carboxylate and thus, there is no side reaction such as dehydration which is shown in conventional method.

Cyanation in the present invention is conducted with 1.0~5.0 equivalents of a cyanation reagent at the temperature of 0~100° C. for 0.5~5 hours. The cyanation reagent is selected from the group consisting of potassium cyanide, sodium cyanide and alkyl ammonium cyanide having 1~4 carbon atoms. Solvent used in cyanation can be water or a mixture of water and organic solvent. The organic solvent is selected from the group consisting of acetonitrile, dichloro methane, chloroform, linear or branched alcohol having 1~4 carbon atoms, tetrahydrofuran, benzene and toluene.

Esterification in the present invention is conducted by reacting cyanation reaction mixture with an acid such as sulfuric acid, hydrochloric acid, phosphoric acid or nitric acid, followed by concentration of solvent prior to reaction with ROH at 0~100° C. wherein R represents linear or branched alkyl group having 1~4 carbon atoms or benzyl group.

(R)-4-cyano-3-hydroxybutyric acid ester with over 90% of yield and 99.8% of optical purity is obtained by performing the process described in the present invention.

The following examples are intended to be illustrative of the present invention and should not be construed as limiting the scope of this invention defined by the appended claims.

EXAMPLE 1

Preparation of (S)-3-Acetoxy-4-bromobutyric Acid

To a 2 l of three-necked flask equipped with reflux condenser, thermometer and mechanical stirrer were charged (S)-3-hydroxy-γ-butyrolactone (102 g) and 30% of hydrobromic acid in acetic acid (675 g, 2.5 eq.). The mixture was stirred at 40° C. for 3 hours. After cooling the reaction mixture, methylene chloride (1000 ml) was added to it. The reaction mixture was washed with aqueous solution of sodium acetate. The organic layer was separated, dried over magnesium sulfate, and concentrated to afford (S)-3-acetoxy-4-bromobutyric acid (213 g, 95%).

$^1$H-NMR (D$_2$O, ppm): δ 2.1 (S, 3H, CH$_3$COO), 2.8~2.9 (dd, 2H, CH$_2$COOH), 3.5~3.6 (dd, 2H, BrCH$_2$CH), 5.3~5.4 (m, 1H, BrCH$_2$CH).

EXAMPLE 2

Preparation of (S)-3,4-Epoxybutyric Acid Sodium Salt

To a 5 l flask was charged (S)-3-acetoxy-4-bromobutyric acid obtained from example 1. 1N aqueous solution of sodium hydroxide (3 l, 3 mol) was slowly added by keeping the temperature below 0° C. The reaction mixture was stirred at 0° C. for 1 hour. Fairly pure (S)-3,4-epoxybutyric acid sodium salt was detected by NMR.

$^1$H-NMR (D$_2$O, ppm): δ 2.3~2.5 (m, 2H, CH$_2$—CO$_2$Na), 2.6~2.9 (m, 2H), 3.2~3.3 (m, 1H); $^{13}$C-NMR (D$_2$O, ppm): δ 40.87 (—CH$_2$—CO$_2$Na), 48.24 (4-CH$_2$), 51.08 (3-CH), 179.41 (—CO$_2$Na).

EXAMPLE 3

Preparation of (S)-3,4-Epoxybutyric Acid Potassium Salt

To a 5 l flask was charged (S)-3-acetoxy-4-bromobutyric acid obtained from example 1. 1N aqueous solution of potassium hydroxide (3 l, 3 mol) was slowly added while keeping the temperature below 0° C. The reaction mixture was stirred for 1 hour at 0° C. Fairly pure (S)-3,4-epoxybutyric acid potassium salt was detected by NMR.

$^1$H-NMR (D$_2$O, ppm): δ 2.3~2.5 (m, 2H, CH$_2$—CO$_2$K), 2.6~2.9 (m, 2H), 3.2~3.3 (m, 1H); $^{13}$C-NMR (D$_2$O): δ 40.87 (—CH$_2$—CO$_2$K), 48.24 (4-CH2), 51.08 (3-CH), 179.41 (—CO$_{2K}$).

EXAMPLE 4

Preparation of (S)-3,4-Epoxybutyric Acid Calcium Salt

To a 2 l of three-necked flask equipped with thermometer, pH meter and mechanical stirrer were charged distilled water (1 l), (S)-3-acetoxy-4-bromobutyric acid (90 g, 0.4 mol) and calcium hydroxide (45 g, 0.6 mol). The reaction mixture was stirred at 0~5 for 2 hours to afford (S)-3,4-epoxybutyric acid calcium salt Over 99% of conversion was detected by NMR.

$^1$H-NMR (D$_2$O, ppm): δ 2.3~2.5 (m, 2H, CH$_2$—CO$_2$Ca), 2.5~2.8 (m, 2H, 4H), 3.2~3.3 (m, 1H, 3-H).

EXAMPLE 5

Preparation of (S)-3,4-Epoxybutyric Acid Tetrabutylammonium Salt

To a 2 l of three-necked flask equipped with thermometer, pH meter and mechanical stirrer were charged distilled water (1 l), (S)-3-acetoxy-4-bromobutyric acid (90 g, 0.4 mol) and tetrabutylammonium hydroxide, 1.0 M in methanol (1.2 l, 1.2 mol). The reaction mixture was stirred at 0~5° C. for 2 hours to afford (S)-3,4-epoxybutyric acid tetrabutyl ammonium salt. Over 99% of conversion was detected by NMR.

$^1$H-NMR (D$_2$O, ppm): δ 2.2~2.3 (m, 2H, CH$_2$—CO$_2$NBu$_1$), 2.5~2.8 (m, 2H, 4-H), 3.2~3.3 (m, 1H, 3-H).

EXAMPLE 6

Preparation of (S)-3,4-Epoxybutyric Acid Triethylamnie Salt

To a 2 l of three-necked flask equipped with thermometer, pH meter and mechanical stirrer were charged distilled water (1 l), (S)-3-acetoxy-4-bromobutyric acid (90 g, 0.4 mol) and triethylamine (12 g, 1.2 mol). The reaction mixture was stirred at 0~5° C. for 2 hours to afford (S)-3,4-epoxybutyric acid triethylamine salt. Over 99% of conversion was detected by NMR.

$^1$H-NMR (D$_2$O, ppm): δ 2.2~2.4 (m, 2H, CH$_2$—CO$_2$NEt$_3$), 2.5~2.8 (m, 2H, 4-H), 3.1~3.2 (m, 1H, 3-H).

EXAMPLE 7

Preparation of (S)-3,4-Epoxybutyric Acid Diisopropylamine Salt

To a 2 l of three-necked flask equipped with thermometer pH meter and mechanical stirrer were charged distilled water (1 l), (S)-3-acetoxy-4-bromobutyric acid (90 g, 0.4 mol) and diisopropylamine (121 g, 1.2 mol). The reaction mixture was stirred at 0~5° C. for 2 hours to afford (S)-3,4-epoxybutyric acid diisopropylamine salt. Over 99% of conversion was detected by NMR.

$^1$H-NMR (D$_2$O, ppm): δ 2.2~2.3 (m, 2H, CH$_2$—CO$_2$NH$_2$iPr$_2$), 2.5~2.8 (m, 2H, 4-H) 3.1~3.2 (m, 1H, 3-H).

EXAMPLE 8

Preparation of (S)-3,4-Epoxybutyric Acid t-Butylamine Salt

To a 2 l of three-necked flask equipped with thermometer, pH meter and mechanical stirrer were charged distilled water (1 l), (S)-3-acetoxy-4-bromobutyric acid (90 g, 0.4 mol) and t-butylamine (88 g, 1.2 mol). The reaction mixture was stirred at 0~5° C. for 2 hours to afford (S)-3,4-epoxybutyric acid t-butylamine salt. Over 99% of conversion was detected by NMR.

$^1$H-NMR (D$_2$O, ppm): δ 2.1~2.4 (m, 2H, CH$_2$—CO$_2$NH$_3$Bu–t), 2.5~2.8 (m, 2H, 4-H), 3.1~3.2 (m, 1H, 3-H).

EXAMPLE 9

Preparation of (R)-4-Cyano-3-hydroxybutyric Acid

30% of aqueous sodium cyanide solution (163 g, 1.0 mol) was added to (S)-3,4-epoxybutyric acid sodium salt obtained from example 2 dissolved in water. The reaction mixture was stirred at 60° C. for 3 hours. Over 99% of conversion was detected by NMR.

$^1$H-NMR (D$_2$O, ppm): δ 2.3 (d, 2H, CH$_2$), 2.5~2.7 (m, 2H, CH$_2$), 4.1 (m, 1H, CH—OH).

The reaction mixture containing (R)-4-cyano-3-hydroxy butyric acid sodium salt was acidified to pH 1 with concentrated sulfuric acid. The reaction mixture was condensed, dissolved in ethanol and filtered. The filtrate was concentrated to give (R)-4-cyano-3-hydroxybutyric acid which was used for esterification without further purification.

$^1$H-NMR (D$_2$O, ppm): δ 2.5~2.8 (m, 4H, 2CH$_2$), 4.3 (m, 1H, CH—OH).

EXAMPLE 10

Preparation of (R)-4-Cyano-3-hydroxybutyric Acid

Tetraethylammonium cyanide (156 g, 1.0 mol) was added into (S)-3,4-epoxybutyric acid sodium salt (1.0 mol) obtained front example 2 dissolved in water. The reaction mixture was stirred at 60° C. for 3 hours to prepare (R)-4-cyano-3-hydroxy butyric acid sodium salt. Over 99% of conversion was detected by NMR.

$^1$H-NMR (D$_2$O, ppm): δ 2.3 (d, 2H, CH$_2$), 2.5~2.7 (m, 2H, CH$_2$), 4.1 (m, 1H, CH—OH).

The reaction mixture containing (R)-4-cyano-3-hydroxybutyric acid sodium salt was acidified to pH 1 with concentrated sulfuric acid. The reaction mixture was condensed, dissolved in ethanol and filtered. The filtrate was concentrated to give (R)-4-cyano-3-hydroxybutyric acid which was used for esterification without further purification.

$^1$H-NMR (D$_2$O, ppm): δ 2.5~2.8 (m, 4H, 2CH$_2$), 4.3 (m, 1H, CH—OH).

EXAMPLE 11

Preparation of (R)-4-Cyano-3-hydroxybutyric Acid

30% aqueous sodium cyanide (163 g, 1.0 mol) was added into (S)-3,4-epoxybutyric acid calcium salt (1.0 mol) obtained from example 4 dissolved in water. The reaction mixture was stirred at 60° C. for 3 hours to prepare (R)-4-cyano-3-hydroxybutyric acid calcium salt Over 99% of conversion was detected by NMR.

Concentrated sulfuric acid was added into the reaction mixture to adjust pH 1. The reaction was concentrated in vacuo. The residue was dissolved in ethanol and filtered. The filtrate was concentrated to afford (R)-4-cyano-3-hydroxybutyric acid which was used for esterification without further purification.

$^1$H-NMR (D$_2$O, ppm): δ 2.5~2.8 (m, 4H, 2CH$_2$), 4.3 (m, 1H, CH—OH).

EXAMPLE 12

Preparation of (R)-4-Cyano-3-hydroxybutyric Acid

30% aqueous sodium cyanide (163 g, 1.0 mol) was added into (S)-3,4-epoxybutyric acid tetrabutylammonium salt (1.0 mol) obtained from example 5 dissolved in water. The reaction mixture was stirred at 60° C. for 3 hours to prepare (R)-4-cyano-3-hydroxybutyric acid tetrabutylammonium salt. Over 99% of conversion was detected by NMR.

Concentrated sulfuric acid was added into the reaction mixture to adjust pH 1. The reaction was concentrated in vacuo. The residue was dissolved in ethanol and filtered. The filtrate was concentrated to afford (R)-4-cyano-3-hydroxybutyric acid which was used for esterification without further purification.

$^1$H1-NMR (D$_2$O, ppm): δ 2.5~2.8 (m, 4H, 2CH$_2$), 4.3 (m, 1H, CH—OH).

EXAMPLE 13

Preparation of (R)-Cyano-3-hydroxybutyric Acid Methyl Ester (R)-4-cyano-3-hydroxybutyric acid (1.0 mol) in methanol (500 ml) and conc. sulfuric acid (5 g) were refluxed for 5 hours. The reaction mixture was neutralized with sodium carbonate and filtered. The filtrate was concentrated in vacuo to afford (R)-4-cyano-3-hydroxybutyric acid methyl ester (130 g, 91%).

$^1$H-NMR (D$_2$O, ppm): δ 2.6~2.7 (m, 4H, 2CH$_2$), 3.7 (s, 3H, OCH$_3$), 4.4 (m, 1H, CH—OH).

EXAMPLE 14

Preparation of (R)-Cyano-3-hydroxybutyric Acid Ethyl Ester (R)-4-cyano-3-hydroxybutyric acid (1.0 mol) in ethanol (500 ml) and conc. sulfuric acid (5 g) were refluxed for 5 hours. The reaction mixture was neutralized with sodium carbonate ancd filtered. The filtrate was concentrated in vacuo to afford (R)-4-cyano-3-hydroxybutyric acid ethyl ester (141 g, 90%).

$^1$H-NMR (D$_2$O, ppm): δ 1.2 (t, 3H, CH$_3$), 2.5~2.6 (m, 4H, 2CH$_2$), 4.1 (q, 2H, OCH$_2$), 4.3 (m, 1H, CH—OH).

EXAMPLE 15

Preparation of (R)-Cyano-3-hydroxybutyric Acid Isopropyl Ester (R)-4-cyano-3-hydroxybutyric acid (1.0 mol) in isopropanol (500 ml) and conc. sulfuric acid (5 g) were refluxed for 5 hours. The reaction mixture was neutralized with sodium carbonate and filtered. The filtrate was concentrated in vacuo to afford (R)-4-cyano-3-hydroxybutyric acid isopropyl ester (163 g, 90%).

$^1$H-NMR (D$_2$O, ppm): δ 1.4 (d, 6H, 2CH$_3$), 2.6 (m, 4H, 2CH$_2$), 4.4 (m, 1H, CH—OH), 5.1 (m, 1H, CH—(CH$_3$)$_2$).

EXAMPLE 16

Preparation of (R)-Cyano-3-hydroxybutyric Acid Isobutyl Ester (R)-4-cyano-3-hydroxybutyric acid (1.0 mol) in isobutanol (500 ml) and conc. sulfuric acid (5 g) were refluxed for 5 hours. The reaction mixture was neutralized with sodium carbonate and filtered. The filtrate was concentrated in vacuo to afford (R)-4-cyano-3-hydroxybutyric acid isobutyl ester (157 g, 92%).

$^1$H-NMR (D$_2$O, ppm): δ 0.8 (d, 6H, 2CH$_3$), 1.9 (m, 1H, CH—(CH$_3$)$_2$), 2.6~2.7 (m, 4H, 2CH$_2$), 3.9 (d, 2H, O—CH$_2$), 4.3 (m, 1H, CH—OH).

EXAMPLE 17

Preparation of (R)-Cyano-3-hydroxybutyric Acid Benzyl Ester

Benzylalcohol (216 g, 2 eq.) and conc. sulfuric acid (5 g) were added to (R)-4-cyano-3-hydroxybutyric acid (1.0 mol) dissolved in acetonitrile (500 ml) and refluxed for 5 hours. The reaction mixture was neutralized with sodium carbonate and filtered. The filtrate was concentrated in vacuo to afford (R)-4-cyano-3-hydroxybutyric acid benzyl ester (157 g, 92%) which was purified by column chromatography on a silica gel.

$^1$H-NMR (D$_2$O, ppm): δ 2.6~2.7 (m, 4H, 2CH$_2$), 4.3 (m, 1H, CH—OH), 5.2 (s, 2H, CH,—Ph), 7.2~7.3 (m, 5H, Ph)

The process for preparing (R)-4-cyano-3-hydroxybutyric acid from (S)-3,4-epoxybutyric acid salt by performing cyanation and sequential esterification described in the present invention provides less by-products, much faster reaction time and higher yield than conventional methods. And also it provides various ester compounds by esterification.

What is claimed is:

1. A process for the preparation of (R)-4-cyano-3-hydroxybutyric acid ester expressed by the formula (1) which comprises:

(A) cyanation of (S)-3,4-epoxybutyric acid salt expressed by the formula (2) to afford the compound expressed by the formula (3); and (B) esterification of the compound expressed by the formula (3),

(2)

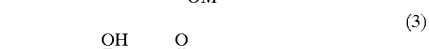

(3)

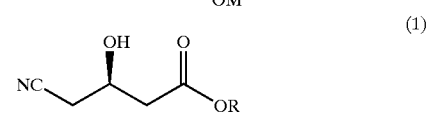

(1)

wherein M represents an alkali metal atom, an alkaline earth metal atom or an alkylammonium ion having 1~4 carbon atoms; and R represents a linear or branched alkyl group having 1~4 carbon atoms or a benzyl group.

2. The process of claim 1, wherein the reagent in cyanation is selected from the group consisting of sodium cyanide, potassium cyanide and alkylammonium cyanide having 1~4 carbon atoms.

3. The process of claim 1, wherein the solvent in cyanation is water or a mixture of water and organic solvent.

4. The process of claim 3, wherein the said organic solvent is selected from the group consisting of acetonitrile, dichloro methane, chloroform, linear or branched alcohol with 1~4 carbon atoms, tetrahydrofuran, benzene and toluene.

5. The process of claim 1, wherein the cyanation is conducted at the temperature of 0~100° C.

* * * * *